United States Patent [19]

Ogino

[11] Patent Number: 5,471,294
[45] Date of Patent: Nov. 28, 1995

[54] FLOW IMAGING CYTOMETER

[75] Inventor: Shinichi Ogino, Hyogo, Japan

[73] Assignee: TOA Medical Electronics Co., Ltd., Hyogo, Japan

[21] Appl. No.: 315,183

[22] Filed: Sep. 29, 1994

Related U.S. Application Data

[63] Continuation of Ser. No. 882,704, May 14, 1992, abandoned.

[30] Foreign Application Priority Data

Oct. 24, 1991 [JP] Japan ................... 3-277560

[51] Int. Cl.$^6$ .......................... G01N 21/64; G01N 21/05
[52] U.S. Cl. ...................... 356/73; 356/39; 250/461.2
[58] Field of Search ................... 356/39, 72, 73, 356/318, 417; 250/461.2, 458.1; 435/287, 291, 808

[56] References Cited

U.S. PATENT DOCUMENTS

| | | | |
|---|---|---|---|
| 3,705,755 | 12/1972 | Baer | 356/444 X |
| 3,825,325 | 7/1974 | Hartley et al. | 356/301 |
| 3,950,649 | 4/1976 | Yonekubo | 356/225 X |
| 4,088,407 | 5/1978 | Schoeffel et al. | 356/317 |
| 4,099,872 | 7/1978 | White | 356/318 |
| 4,203,670 | 5/1980 | Bromberg | 356/318 |
| 4,338,024 | 7/1982 | Bolz et al. | 356/23 |
| 4,345,837 | 8/1982 | Kallet | 356/317 |
| 4,609,286 | 9/1986 | Sage, Jr. | 356/73 |
| 4,673,289 | 6/1987 | Gaucher | 356/72 |
| 4,750,837 | 6/1988 | Gifford et al. | 356/318 |
| 4,772,125 | 9/1988 | Yoshimura et al. | 356/237 |
| 4,988,619 | 1/1991 | Pinkel | 435/30 |
| 5,018,866 | 5/1991 | Osten | 356/417 |
| 5,053,626 | 10/1991 | Tillotson | 356/417 |
| 5,159,397 | 10/1992 | Kosaka et al. | 356/73 |
| 5,159,398 | 10/1992 | Maekawa et al. | 356/73 |

FOREIGN PATENT DOCUMENTS

| | | |
|---|---|---|
| 0466168 | 1/1992 | European Pat. Off. |
| 3603905 | 8/1986 | Germany. |
| 3705876 | 4/1988 | Germany. |
| 2238612 | 6/1991 | United Kingdom. |

OTHER PUBLICATIONS

Laser und Optoelektronik, vol. 21, No. 1, Feb., 1989, Stuttgart, Germany, pp. 64–68, W. J. Hiller et al.: "Schnelle Bildaufzeichnung mit CCD–Kameras und Gepulsten LEDs–High Speed Image Recording".

Primary Examiner—Robert J. Warden
Assistant Examiner—Theresa T. Snider
Attorney, Agent, or Firm—Pearne, Gordon, McCoy & Granger

[57] ABSTRACT

Disclosed is a flow imaging cytometer having a flow cell one side of which is irradiated with excitation light, in which wavelength selecting means for reflecting excitation light and transmitting fluorescence or reflecting means for reflecting excitation light is provided on the side of the flow cell opposite the side irradiated, thereby increasing the intensity of the excitation light so that the intensity of fluorescence emitted from an irradiated cell is increased. It is possible to pick up the fluorescent images at all times. The cytometer includes a light source for emitting the excitation light, dichroic mirrors which construct the wavelength selecting means, a photomultiplier for detecting fluorescence from irradiated cells, and a cell flow-by decision circuit which, based upon a detection signal from the photomultiplier, determines whether a detected cell of interest is suited to pick-up of a fluorescent image and produces a prescribed control signal for controlling an electronic shutter.

12 Claims, 7 Drawing Sheets

FLOW IMAGING CYTOMETER

This is a continuation of application Ser. No. 07/882,704, filed May 14, 1992, now abandoned.

BACKGROUND OF THE INVENTION

1. Field of the Invention

This invention relates to a flow imaging cytometer for picking up the fluorescent images of cells.

2. Description of the Prior Art

A laser light source often is used as an excitation light source in flow cytometers for measuring fluorescence emitted from unstained cells or from cells that have been treated with a fluorescent stain. The reason for employing such a light source is that use of a laser makes it possible to narrow down the zone measured, as a result which the intensity of irradiation per unit area in the measurement zone can be increased to strengthen the intensity of the fluorescence obtained from the irradiated cells.

A problem which arises when using a laser is that the excitation wavelength is limited to a specific wavelength, as a consequence of which a limitation is placed upon the fluorescent stain solutions that can be used. In addition, a laser light source is large in size and high in cost.

A method adopted in an effort to solve these problems involves using an xenon lamp or the like as the excitation light source and selecting the wavelength of the excitation light by using an interference filter as a filter which selects the excitation light. However, since the irradiated zone cannot be narrowed down in the manner made possible by a laser, a high fluorescent intensity is not obtained. The problem involving the intensity of the excitation light is conspicuous in an apparatus for picking up a fluorescent image, as set forth in the specification of Japanese Patent Application Nos. 3-33151, 3-33189, 3-33137 and 3-33138. The following methods have been adopted in order to intensify fluorescence for the sake of obtaining the fluorescent images of cells:

1. An excitation light source having a high light-emission intensity is used.
2. The excitation light is narrowed down to the smallest zone possible.
3. Weak fluorescence is intensified by an image intensifier, which is a photomultiplier element.

If the intensity of the fluorescence emitted from a cell is low, however, applying excessive amplification by an image intensifier results in a lower S/N ratio due to photoelectric noise. The resulting drawback is a deterioration in image quality. This means that there is a limit upon the maximum mu-factor that can be used, and hence the intensity of the fluorescence necessary for picking up the fluorescent image of a cell is inadequate.

SUMMARY OF THE INVENTION

Accordingly, an object of the present invention is to provide a flow imaging cytometer in which the intensity of fluorescence needed for picking up the fluorescent image of a cell can be sufficiently increased if the intensity of light from an excitation light source is weak.

According to the present invention, the foregoing object is attained by providing a flow imaging cytometer having a flow cell one side of which is irradiated with excitation light, in which wavelength selecting means for reflecting excitation light and transmitting fluorescence or reflecting means for reflecting excitation light is provided on the side of the flow cell opposite the side irradiated, thereby increasing the intensity of the excitation light so that the intensity of fluorescence emitted from a cell is increased.

Other features and advantages of the present invention will be apparent from the following description taken in conjunction with the accompanying drawings, in which like reference characters designate the same or similar parts throughout the figures thereof.

DETAILED DESCRIPTION OF THE PREFERRED EMBODIMENTS

Preferred embodiments of the present invention will now be described in detail with reference to the accompanying drawings with reference to the drawings, a single arrow (→) indicates excitation light, and a double arrow (→→) indicates fluorescence light, unless specifically stated otherwise.

Figure 1:
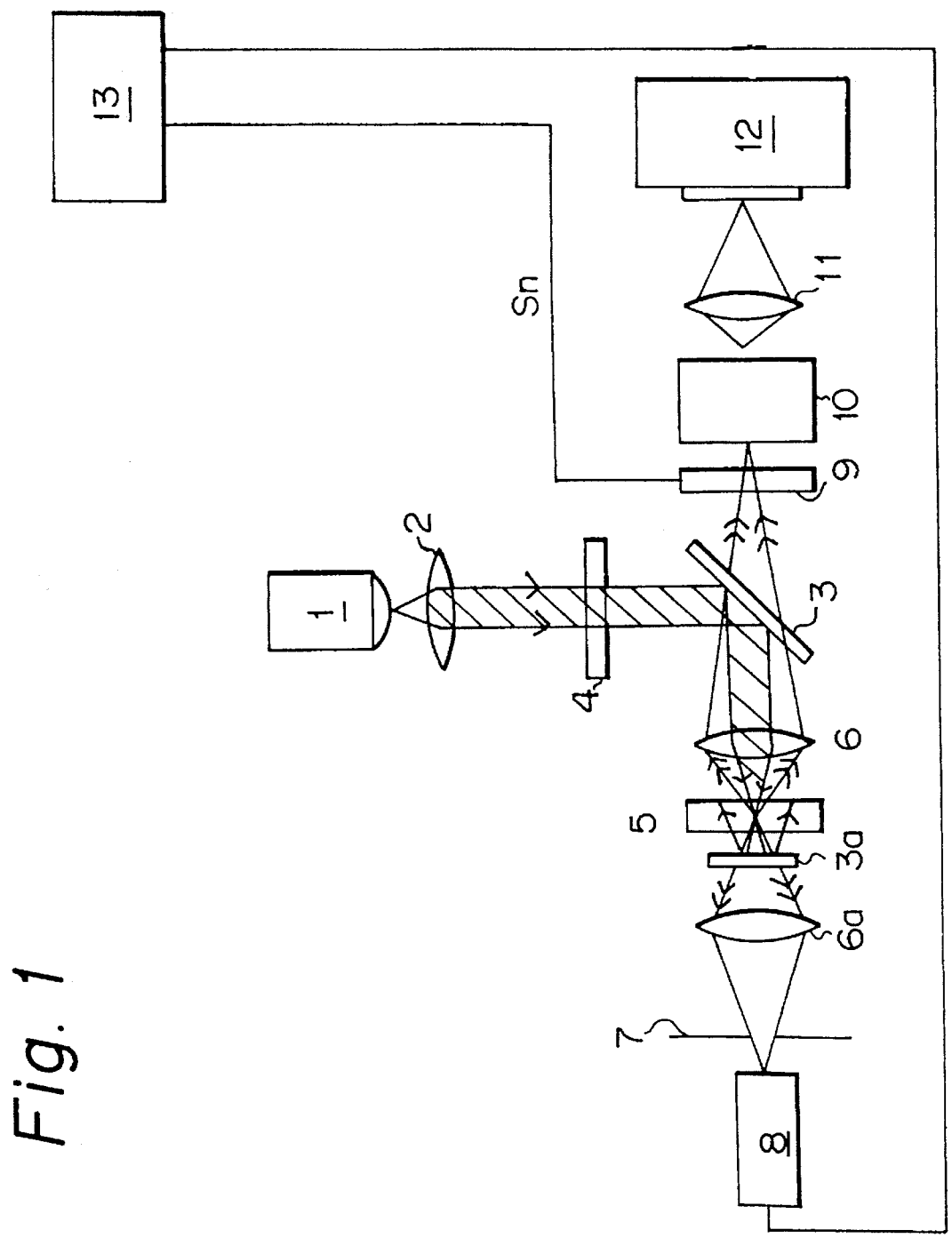
FIG. 1 is a block diagram illustrating the construction of a first embodiment of a flow imaging cytometer according to the present invention.

FIG. 1 is a block diagram illustrating the construction of a first embodiment of a flow imaging cytometer according to the present invention. The apparatus includes a flow cell 5 formed to include a flat flow path for causing a specimen solution containing cells to flow as a flat stream. The apparatus is adapted to pick up the images of specific cells flowing through the cell. In accordance with a feature of the invention, the cells which flow through the flow cell 5 are monitored at all times and only the fluorescent images of cells which emit fluorescence are selectively picked up. The embodiment of FIG. 1 (and of FIG. 7, described later)

represents an apparatus of the incident-light type.

The apparatus further includes a light source 1 for inducing fluorescence. The light source 1, which uses an xenon lamp of the continuously light-emitting type and emits excitation light, acts as a light source for image pick-up. A collimator lens 2 disposed in front of the excitation light source 1 receives the light from the light source 1 and renders the light parallel. A filter 4 for selecting excitation light receives the collimated light and selects a wavelength of light through which the cells flowing through the flow cell 5 will pass. More specifically, the filter 4 selects a wavelength best suited for the cells of interest or for the fluorescent stain solution and allows the light of the selected wavelength to pass through.

Figure 2:
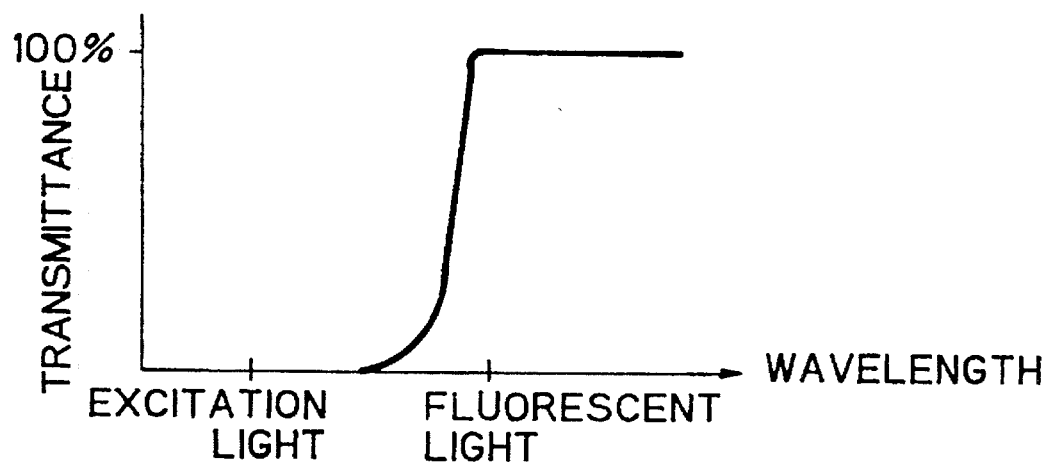
FIG. 2 is a characteristic diagram showing the wavelength transmittance of a dichroic mirror serving as wavelength selecting means.

A dichroic mirror 3 on one side of the flow cell 5 receives the excitation light that has passed through the selective filter 4 and reflects the excitation light in a predetermined direction so that it will impinge upon an objective lens 6 on one side of the flow cell 5. It should be noted that the characteristic of the dichroic mirror 3 is such that fluorescent light will pass through it. A second dichroic mirror 3a on the other of the flow cell 5 selects and transmits fluorescence emitted by cells in the flow cell 5 but reflects the excitation light. FIG. 2 illustrates an example of the wavelength-transmittance characteristics of the dichroic mirrors 3, 3a.

Figure 3:
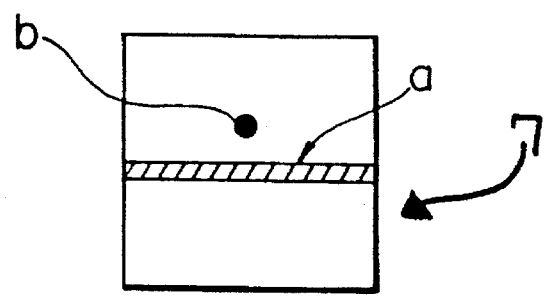
FIG. 3 is a diagram showing the relationship between an image pick-up area and a slit in a flow cell.

An objective lens 6a on the other side of the flow cell 5 converges and condenses the fluorescent light emitted by cells and introduces the condensed light to a photomultiplier 8 serving as detecting means. Disposed between the objective lens 6a and the photomultiplier 8 on the light-entrant side of the photomultiplier is a slit 7 which limits the zone for detecting the fluorescence emitted from cells in the image pick-up area of the flow cell 5. As shown in FIG. 3, the slit 7 has a light transmitting portion, a, one side of which preferably coincides with a width of 150 µm possessed by the visual field of a video camera 12. The other side of the slit 7 preferably has a width of about 20 µm so as to conform to the flow cell 5. Consequently, it will suffice if the dimensions of the objective lens 6a are 0.2×1.5 mm if the objective lens 6a used has a magnification of 10×, and 0.8×6 mm if the objective lens 6a used has a magnification of 40×. Accordingly, the dimensions of the light transmitting portion, a, of the slit 7 would be 20×150 µm, and the dimensions of a fluorescent image pick-up area, b, of the slit 7 would be 150×150 µm.

A cell flow-by decision circuit 13 applies prescribed processing to the signal outputted by the photomultiplier 8 and determines whether a detected cell is a cell of interest. If the detected cell is a cell of interest, the decision circuit 13 produces a shutter-actuating trigger signal, Sn, to actuate an electronic shutter 9.

Figure 8:
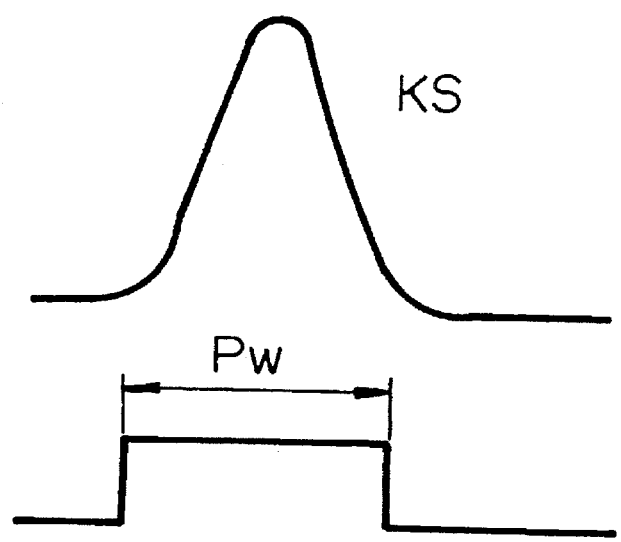
FIG. 8 is a diagram for describing an example of signal processing in a cell flow-by decision circuit.
Figure 9:
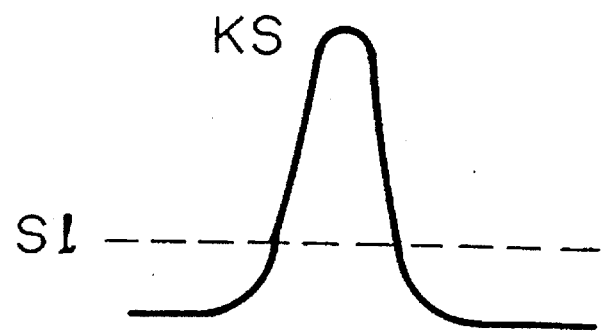
FIG. 9 is a diagram for describing another example of signal processing in the cell flow-by decision circuit.

FIGS. 8 and 9 illustrate examples of the signal processing performed by the cell flow-by decision circuit 13. Specifically, a cell is determined to be a cell of interest if the pulse width of a fluorescent signal V,KS, emitted by a cell is a predetermined pulse width, Pw, if signal strength exhibits a value greater than a predetermined threshold level Sl, or if both of these conditions are satisfied.

The electronic shutter 9 selects which light received by the objective lens 6 from the fluorescent light emitted by a cell is allowed to impinge upon an image intensifier 10. The electronic shutter 9 is controlled by the cell flow-by decision circuit 13. The period of time during which the,electronic shutter 9 is opened (released) is decided by the flow velocity of cells used as a sample. For example, if the flow velocity of the cells is 1 m/sec, then the shutter 9 must be opened for about 1 µm. If the shutter 9 is opened for longer than this time period, the fluorescent image formed on the image intensifier 10 will move owing to the flow and a still picture will no longer be obtained.

The image intensifier 10 is a photomultiplier element in which light incident upon its photoelectric surface is amplified by a factor of $10^3$ to $10^6$ before being delivered to a side thereof having a fluorescent surface. An arrangement can be adopted in which the image intensifier 10 has a built-in electronic shutter function, in which case the electronic shutter 9 would be separately provided.

An image-forming lens 11, which is disposed between the image intensifier 10 and the video camera 12, converges and condenses the light indicative of the image outputted by the fluorescence surface of the image intensifier 10 and forms the resulting image on a Charge Coupled Device (CCD) in the video camera 12.

The operation of the apparatus will now be described.

Excitation light produced by the light source 1 for inducing fluorescence passes through the collimator lens 2 and the resulting collimated light is then reflected by the dichroic mirror 3. The reflected light is converged by the objective lens 6 and constantly irradiates the flow cell 5. Only fluorescence emitted from a cell within the flow cell 5 passes through the dichroic mirror 3a and is transmitted by the slit 7, after which it impinges upon the photomultiplier 8. The latter produces a detection signal that is applied to the cell flow-by decision circuit 13, which determines whether the signal is indicative of a cell of interest. If the detected cell is a cell of interest, the electronic shutter 9 is released by the shutter-actuating trigger, Sn, produced by the decision circuit 13. The component of the excitation light reflected by the dichroic mirror 3a again irradiates the cell in the flow cell 5. Since the distance between the flow cell 5 and the dichroic mirror 3a is sufficiently short, there is almost no time difference between the excitation light which has irradiated the cell directly and the excitation light that has been reflected so as to irradiate the cell, and therefore the cell is irradiated substantially simultaneously. As a consequence, the intensity of the excitation light obtained is equivalent to what would be obtained by irradiating the cell with excitation light having approximately twice the illumination. Since the fluorescence emitted from the cell is isotropic in all directions, the fluorescence from the flow cell 5 impinges also upon the electronic shutter 9 via the objective lens 6 at the same time that the photomultiplier 8 detects the fluorescence signal. If at this time the detected cell is determined to be a cell of interest by the cell flow-by decision circuit 13, the electronic shutter 9 is released so that the fluorescent image of the cell is formed on the photoelectric surface of the image intensifier 10. The fluorescent image is amplified by the image intensifier 10 and is delivered to its fluorescent surface, namely its output surface. The resulting intensified image is formed on the CCD of the video camera 12 by the image-forming lens 11, whereby a fluorescent image of the cell is obtained.

Figure 4:
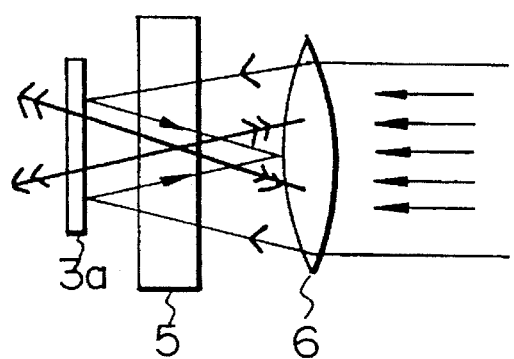
FIG. 4 is a diagram showing an arrangement of optical components in the vicinity of the flow cell.

FIG. 4 is a diagram showing an arrangement of the optical components in the vicinity of the flow cell 5 according to the present invention. As shown in FIG. 4, the excitation light is converged by the objective lens 6 and irradiates the flow cell 5 from the right side in the drawing. The excitation light is reflected by the dichroic mirror 3a on the left side of the flow cell 5 and again irradiates the cells within the flow cell. Meanwhile the fluorescence emitted by the irradiated cells passes through the dichroic mirror 3a so as to impinge upon the photomultiplier 8.

Figure 5:
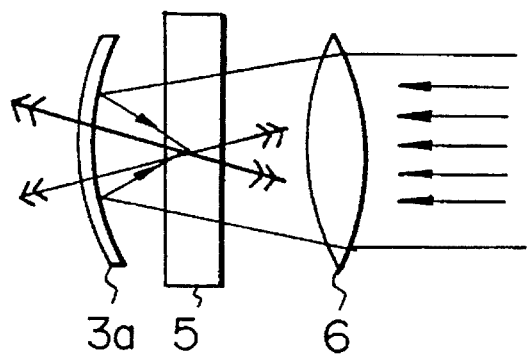
FIG. 5 is a diagram showing an arrangement of optical components in the vicinity of the flow cell in a case where the dichroic mirror is concave.

It should be noted that dichroic mirror 3a used can be one which is concave in shape, as shown in FIG. 5. In such case, if the focal point of the reflected light from the dichroic mirror 3a is placed in the measurement zone of the flow cell 5, then even the excitation light incident upon the periphery of the concave mirror can be converged toward the measurement zone, as a result of which the degree of illumination provided by the excitation light can be increased even further.

Figure 6:
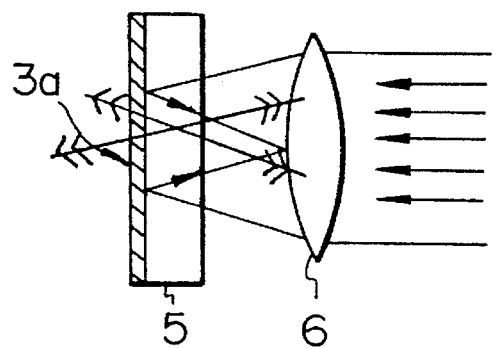
FIG. 6 is a diagram showing an arrangement of optical components in the vicinity of the flow cell in a case where the back surface of the flow cell is provided with a vapor-deposited film serving as wavelength selecting means.

As illustrated in FIG. 6, it is also possible to vapor-deposit a wavelength-selective film on the back surface of the flow cell 5.

Figure 7:
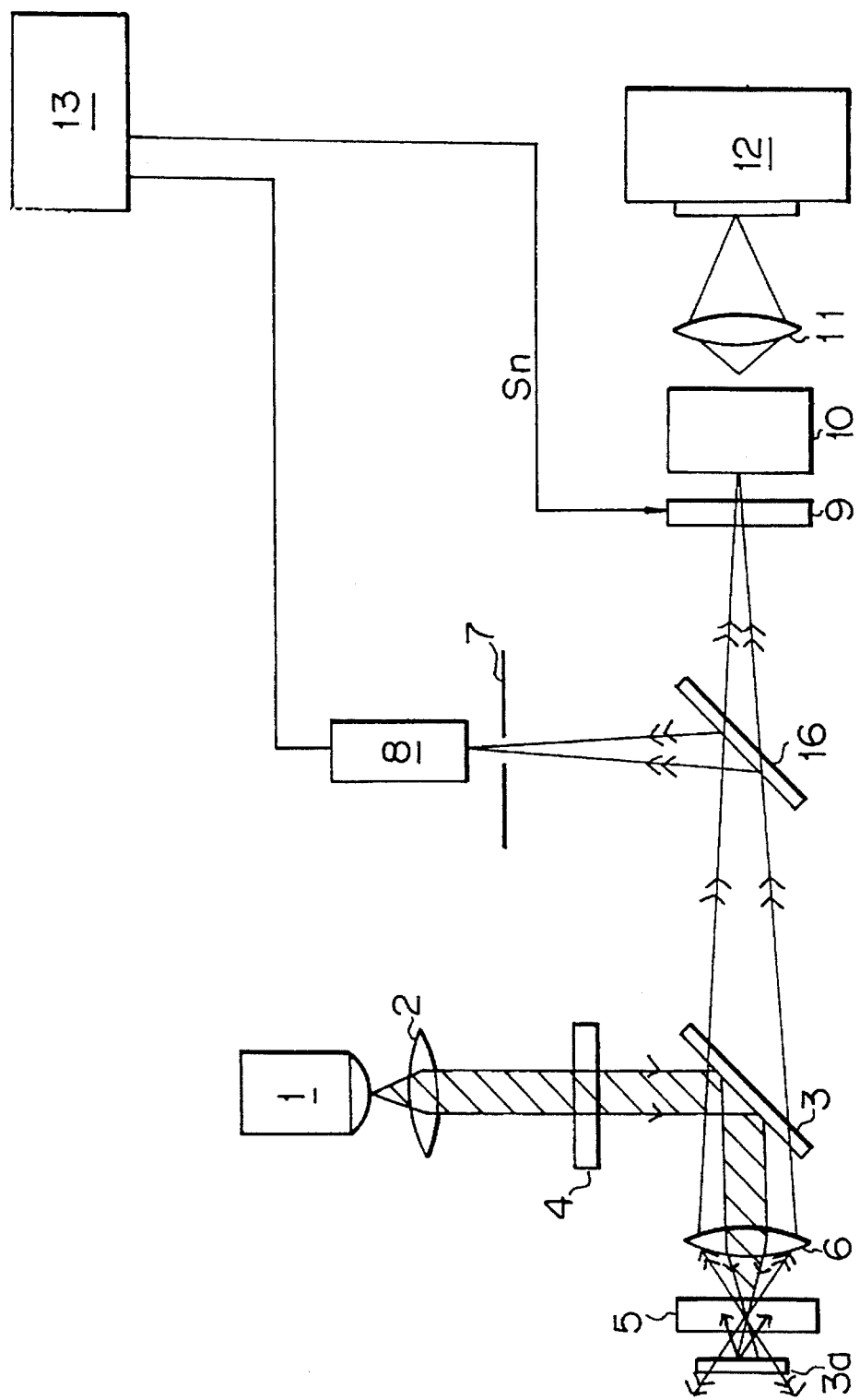
FIG. 7 is a block diagram illustrating the construction of a second embodiment of a flow imaging cytometer according to the present invention.

FIG. 7 is a block diagram illustrating the construction of a second embodiment of a flow imaging cytometer according to the present invention.

This embodiment is simplified in construction by arranging the cell monitoring system and the image pick-up system on the same optic axis. In this case, it is required that a half-mirror 16 be interposed between the dichroic mirror 3 and the electronic shutter 9. Here fluorescent light reflected by the half-mirror 16 is detected by the photomultiplier 8, and fluorescent light transmitted by the half-mirror 16 is picked up and imaged by the image pick-up means 12.

Figure 10:
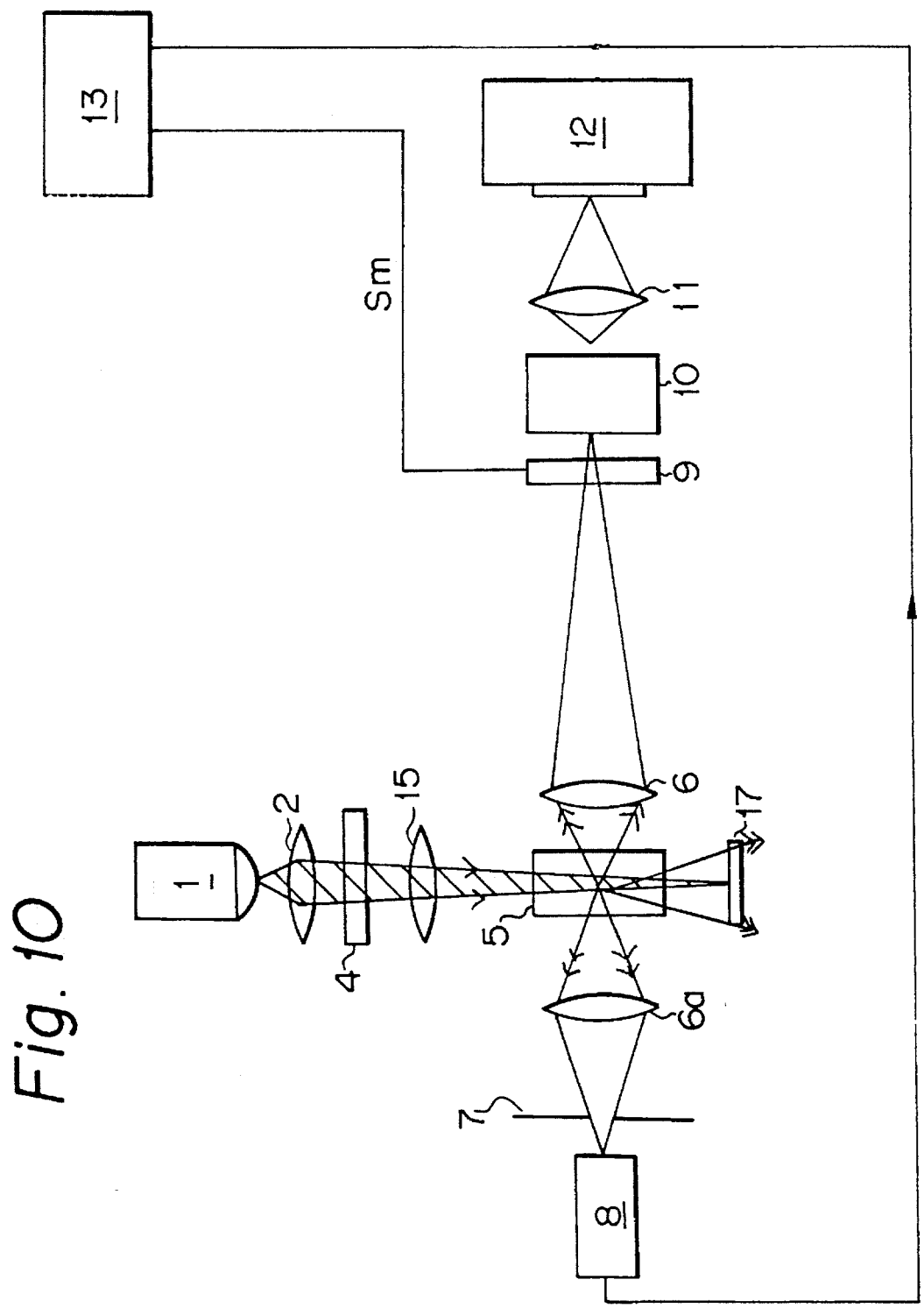
FIG. 10 is a block diagram illustrating the construction of a third embodiment of a flow imaging cytometer according to, the present invention.

FIG. 10 is block diagram illustrating the construction of a third embodiment of a flow imaging cytometer according to the present invention.

In this embodiment, the dichroic mirrors 3, 3a are eliminated by arranging the cell monitoring system and the image pick-up system at right angles to the excitation-light irradiating system. In this arrangement, the dichroic mirrors 3, 3a are replaced by reflecting means 17 as wavelength selecting means in order to measure fluorescence from one side of the cell which emits the fluorescence. To this end, it is required that the reflecting means 17 be disposed on the side of the flow cell 5 opposite the light source 1 which induces the fluorescence. Examples of the reflecting means 17 are a planar mirror or, as in the arrangement of FIG. 5, a concave mirror whose focal point is placed at a position in the measurement zone of the flow cell 5. As for the disposition of the reflecting means 17, it may be placed in the same manner as the dichroic mirror 3a in the arrangement shown in FIGS. 4, 5 and 6.

Figure 11:
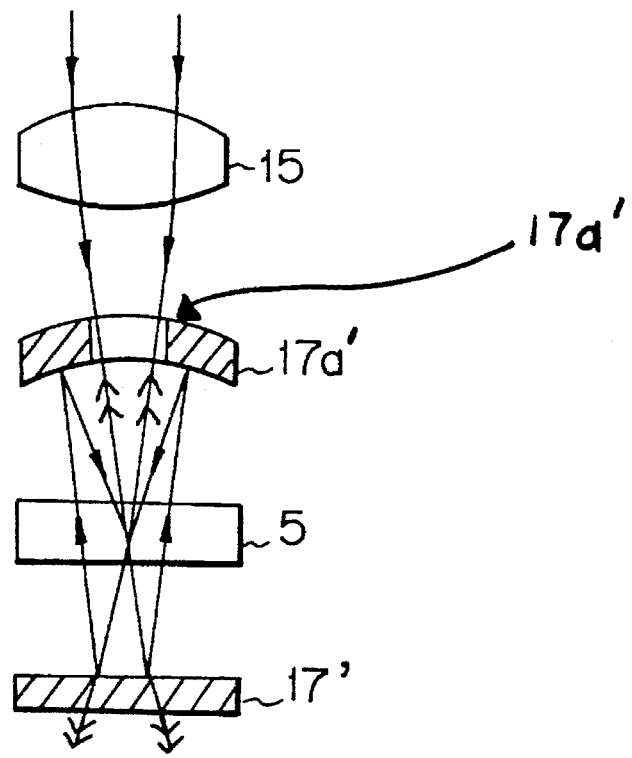
FIG. 11 is a diagram showing an arrangement of optical components in the vicinity of the flow cell in a case where the dichroic mirror is concave according to the third embodiment.
Figure 12:
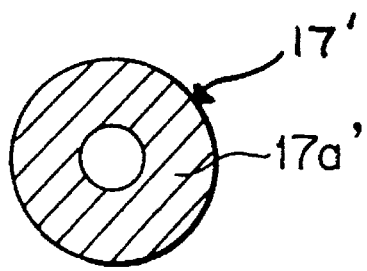
FIG. 12 is a plan view illustrating a circular aperture in a concave mirror.

In still another possible arrangement, a concave mirror 17' having a circular aperture 17a' at its center, as shown in FIG. 11 and FIG. 12, can be provided between an excitation-light converging lens 15 and the flow cell 5. As a result, the excitation light is reflected at the concave surface portion to make possible a further increase in the illumination provided by the excitation light.

Thus, in accordance with the flow imaging cytometer of the present invention, as described above, the entirety of a cell can be irradiated with excitation light owing to reflection of excitation light by wavelength selecting means or reflecting means provided in back of a flat flow path of a specimen solution. In addition, since cells in the specimen solution are irradiated with the excitation light resulting from reflection, the illumination afforded by the excitation light can be doubled in comparison with a case in which the specimen solution is irradiated from only one side. As a result, it is possible to increase the intensity of the fluorescence emitted by the irradiated cells.

As many apparently widely different embodiments of the present invention can be made without departing from the spirit and scope thereof, it is to be understood that the invention is not limited to the specific embodiments thereof except as defined in the appended claims.

What is claimed is:

1. A flow imaging cytometer comprising:

a flow cell through which a specimen solution containing cells to be detected is caused to flow in a state that a sheath liquid surrounds said specimen solution said cells including a cell of interest;

a light source for irradiating a flow zone of the specimen solution in said flow cell with light;

image pick-up means for picking up a still image of the cell of interest in the specimen solution; and image processing means for executing desired data processing based upon a set of image data obtained from said image pick-up means;

wherein fluorescent images of the cells which flow through said flow cell are picked up by said image pick up means and analyzed; and the irradiating light from said light source is light for exciting fluorescence in the cells;

the flow imaging cytometer further comprising:

reflecting means positioned at an opposite side with respect to a light entrant side of the excitation light for reflecting excitation light transmitted by said flow cell during irradiation of said specimen solution and for transmitting the fluorescence emitted by the cells in order to redirect said transmitted excitation light to said specimen solution again so as to enhance the fluorescent images of the cells by the redirected excitation light;

detecting means for detecting the fluorescence light, which is emitted by the cells in said flow cell, separately of said image pick-up means; and decision control means for detecting a cell of interest based upon the detection signal from said detecting means, determining whether the cell of interest requires operation of said image pick-up means, and generating a prescribed control signal for pick-up of the image when the cell of interest requires pick-up of the image.

2. The flow imaging cytometer according to claim 1, wherein said reflecting means has a planar surface.

3. The flow imaging cytometer according to claim 1, wherein said reflecting means has a concave surface.

4. The flow imaging cytometer according to claim 1, wherein said reflecting means is provided in intimate contact with a surface of said flow cell.

5. The flow imaging cytometer according to claim 1, wherein said reflecting means comprises a vapor-deposited film formed on a surface of said flow cell.

6. The flow imaging cytometer according to claim 1, further comprising a second reflecting means located on the excitation light incident side of said flow cell, said second reflecting means having a concave surface provided with an aperture through which irradiating excitation light is allowed to pass.

7. A flow imaging cytometer comprising:

a flow cell through which a specimen solution containing cells to be detected is caused to flow in a state that a sheath liquid surrounds said specimen solution said cells including a cell of interest;

a light source for irradiating a flow zone of the specimen solution in said flow cell with light;

image pick-up means for picking up a still image of the cell of interest in the specimen solution; and image processing means for executing desired data processing based upon image data from said image pick-up means;

the irradiating light from said light source is light for exciting fluorescence in the cells;

wherein fluorescent images of the cells which flow through said flow cell are picked up by said image pickup means and analyzed;

the imaging flow cytometer further comprising:

reflecting means positioned at an opposite side with respect to a light entrant side of the excitation light for reflecting excitation light transmitted by said flow cell during irradiation of said specimen solution and for transmitting the fluorescence emitted by the cells in older to redirect only said transmitted excitation light to said specimen solution again so as to enhance the fluorescent images of the cells by the redirected excitation light;

detecting means for detecting the fluorescence light, which is emitted by the cells in said flow cell, separately of said image pick-up means; and decision control means for detecting a cell of interest based upon the detection signal from said detecting means, determining whether the cell of interest requires operation of said image pick-up means, and generating a prescribed control signal for pick-up of the image when the cell of interest requires pick-up of the image.

8. The flow imaging cytometer according to claim 7, wherein said reflecting means has a planar surface.

9. The flow imaging cytometer according to claim 7, wherein said reflecting means has a concave surface.

10. The flow imaging cytometer according to claim 7, wherein said reflecting means is provided in intimate contact with a surface of said flow cell.

11. The flow imaging cytometer according to claim 7, wherein said wavelength selecting means comprises a vapor-deposited film formed on a surface of said flow cell.

12. The flow imaging cytometer according to claim 7, wherein a second reflecting means having a concave surface provided with an aperture through which irradiating excitation light is allowed to pass is provided on the fluorescence excitation light incident side of said flow cell.

* * * * *